United States Patent
Ehringer et al.

(10) Patent No.: US 7,041,312 B2
(45) Date of Patent: *May 9, 2006

(54) WOUND HEALING COMPOSITIONS AND METHODS OF USE

(75) Inventors: William D. Ehringer, Charlestown, IN (US); Sufan Chien, Floyd Knobbs, IN (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/627,195

(22) Filed: Jul. 25, 2003

(65) Prior Publication Data

US 2004/0137051 A1 Jul. 15, 2004

Related U.S. Application Data

(63) Continuation of application No. 10/397,048, filed on Mar. 25, 2003.

(60) Provisional application No. 60/380,762, filed on May 14, 2002.

(51) Int. Cl.
*A61K 9/127* (2006.01)
(52) U.S. Cl. ...................................... 424/450
(58) Field of Classification Search ................. 424/450
See application file for complete search history.

(56) References Cited

U.S. PATENT DOCUMENTS

| | | | |
|---|---|---|---|
| 5,540,935 A | 7/1996 | Miyazaki et al. | |
| 5,674,528 A | 10/1997 | Ogata et al. | |
| 5,863,556 A * | 1/1999 | Ruckert et al. | 424/450 |
| 6,011,020 A | 1/2000 | Gold et al. | |
| 6,086,851 A | 7/2000 | Boni et al. | |
| 6,399,091 B1 * | 6/2002 | Berthold et al. | 424/443 |
| 6,417,326 B1 * | 7/2002 | Cullis et al. | 530/324 |

FOREIGN PATENT DOCUMENTS

JP 03 236320 * 10/1991

OTHER PUBLICATIONS

Ainscow, E.K., and Brand, M.D. (1999) Top-down control analysis of ATP turnover, glycolysis and oxidative phosphorylation in rat hepatocytes. *Eur. J. Biochem.* 263:671-685.

Arakawa A, Ishiguro S, Ohki K, Tamai M. (1998) Preparation of liposome-encapsulating adenosine triphosphate. *Tohuku J Exp Med* 184:39-47.

(Continued)

*Primary Examiner*—Gollamudi S. Kishore
(74) *Attorney, Agent, or Firm*—Jenkins, Wilson, Taylor & Hunt, P.A.

(57) ABSTRACT

A wound-healing composition comprises a wound-treating component and vesicles. The vesicles comprise a phospholipid which is a stable vesicle former and ATP.

12 Claims, 2 Drawing Sheets

OTHER PUBLICATIONS

Brand, M.D. (1995). Measurement of mitochondrial proton motive force. *In* Bioenergetics, a Practical Approach / Brown, G.C., and Cooper, C.E., eds. Oxford University Press, Oxford. 39-62.

Buck, L.T. and P.W. Hochachka, "Anoxic suppression of $Na^+$-$K^+$-ATPase and constant membrane potential in hepatocytes: support for channel arrest," *Am. J. Physiol.* 265 *Regulatory Integrative Comp. Physiol.* 34:R1020-1025 (1993).

Chien, S., "Metabolic Management" *in Organ Procurement and Preservation for Transplantation*, 2nd ed., Ch. 6, pp. 84-109, Springer, Landes Bioscience, Austin, TX (1997).

Connery, C., G. Hicks, and T. Wang, "Positive Correlation of Functional Recovery and Tissue ATP Levels in the Hypothermically Stored Cardiac Explant," *Surgical Forum*, 41:282-284 (1990).

Eckert, D. and P. Kim, "Mechanisms of Viral Membrane Fusion and Its Inhibition," *Annu. Rev. Biochem.*, 70:777-810 (2001).

Ehringer, W., D. Belcher, S. Wassall, and W. Stillwell, "A comparison of the effects of linolenic (18:3Ω3) and docosahexaenoic (22:6Ω3) acids on phospholipid bilayers," *Chem. Phys. Lipids*, 54:79-88 (1990).

Ehringer, W., D. Belcher, S. Wassall, and W. Stillwell, "A comparison of α-linolenic acid (18:3Ω3) and γ-linolenic acid (18:3Ω6) in phosphatidylcholine bilayers," *Chem. Phys. Lipids*, 57:87-96 (1991).

Fedelšová, M., A. Ziegelhöffer, E-G. Krause, and A. Wallenberger, "Effect of Exogenous Adenosine Triphosphate on the Metabolic State of the Excised Hypothermic Dog Heart," *Circulation Res.*, 24:617-627 (1969).

Fraley, R., R. Straubinger, G. Rule, E.L. Springer, and D. Papahadjopoulos, "Liposome-Mediated Delivery of Deoxyribonucleic Acid to Cells: Enhanced Efficiency of Delivery Related to Lipid Composition and Incubation Conditions," *Biochem.*, 20:6978-6987 (1981).

Fremes, S., J. Zhang, R. Furukawa, D. Mickle, et al., "Adenosine Pretreatment for Prolonged Cardiac Storage," *in J. Thorac. Cardiovas. Surg.*, 110(2):293-301 (1995).

Garrett, F., S. Goel, J. Yasul, and R. Koch, "Liposomes fuse with sperm cells and induce activation by delivery of impermeant agents," *Biochim. Et Biophys. Acta,* 1417:77-88 (1999).

Guo-Xing, X., X. Xing-Hui, L. Fang-Yu, Z. DeLiang, et al., "Adenosine Triphosphate Liposomes: Encapsulation and Distribution Studies," *Pharmaceut. Res.*, 7(5)553-557 (1990).

Hirasawa, H., K. Soeda, Y, Ohtake, S. Oda, et al., "Effects of ATP-$MgCl_2$ and ATP-$Na_2$ Administration on Renal Function and Cellular Metabolism Following Renal Ischemia," *Circulatory Shock,* 16:337-346 (1985).

Hochachka, P.W. and P.L. Lutz, "Mechanism, origin, and evolution of anoxia tolerance in animals," *Comp. Biochem. Phys.*, Part B, 130:435-459 (2001).

Jahn, R. and T.C. Südhof, "Membrane fusion and exocytosis," *Annu. Rev. Biochem.* 68:863-911.

Katori, M. and R. Berne, "Release of Adenosine from Anoxic Hearts. Relationship to Coronary Flow," *Circulation Res.*, 19:420-425 (1966).

Klein, H., J. Schaper, St. Puschmann, Ch. Nienaber, et al., "Loss of canine mycocardial nicotinamide adenine dinucleotides determines the transition from reversible to irreversible ischemic damage of myocardial cells," *Basic Res. Cardiol.*, 76:612-621 (1981).

Kozubek, A., J. Gubernator, E. Przeworska, and M. Stasiuk, "Liposomal drug delivery, a novel approach: PLARosomes," *Acta Biochim. Pol.*, 47(3):639-649 (2000).

Kristensen, S., "Mechanisms of cell damage and enzyme release," *Danish Med. Bull.*, 41(4):423-433 (1994).

McAllister, Jr., H., "Histologic Grading of Cardiac Allograft Rejection: A Quantitative Approach," *J. Heart Transplant*, 9(3):277-282 (1990).

Pagano, R. and J. Weinstein, "Interactions of Liposomes with Mammalian Cells," *Ann. Rev. Biophys. Bioeng.*, 7:435-468 (1978).

Palombo, J., J. Bowers, M. Clouse, A. McCullough, et al., "Hepatic utilization of exogenous necleotide precursors for restoration of ATP after cold ischemia in rats," *Amer. J. Clin. Nutr.*, 57:420-427 (1993).

Pearson, M. and G. Rohrmann, "Transfer, Incorporation, and Substitution of Envelope Fusion Proteins among Members of the *Baculoviridae, Orthomyxoviridae, and Metaviridae* (Insect Retrovirus) Families," *J. Virology*, 76(11)5301-5304 (2002).

Puisieux, F, E. Fattal, M. Lahiani, J. Auger, P. Jouannet, P. Couvreur, and J. Delattre, "Liposomes, an interesting tool to deliver a bioenergetic substrate (ATP) in vitro and in vivo studies," *J Drug Target* 2:443-448 (1994).

Reimer, K., R. Jennings, and M. Hill, "Total Ischemia in Dog Hearts, in Vitro," *in* "High Energy Phosphate Depletion and Associated Defects in Energy Metabolism, Cell Volume Regulation, and Sarcolemmal Integrity," *Circ. Res.*, 49:901-911 (1981).

Schiffelers, R., G. Storm, and I. Bakker-Woudenberg, "Liposome-encapsulated aminoglycosides in pre-clinical and clinical studies," *J. Antimicrob. Chemotherap.*, 48:333-344 (2001).

Siegel, N., W. Glazier, I. Chaudry, K. Gaudio, et al., "Enhanced recovery from acute renal failure by the postischemic infusion of adenine nucleotides and magnesium chloride in rats," *Kidney Int'l,* 17:338-349 (1980).

Stringham, J. Southard, G. Anderson, and F. Belzer, "Mechanisms of ATP Depletion in the Cold-Stored Heart," *Transplantation Proc.*, 23(5):2437-2438 (1991).

Trigiante, G. and W. Huestis, "Selective virus-mediated intracellular delivery of membrane-impermeant coumpounds by means of plasma membrane vesicles," *Antiviral Res.*, 45:211-221 (2000).

Whitman, G., R. Kieval, L. Wetstein, S. Seeholzer, et al., "The Relationship between Global Myocardial Ischemia, Left Ventricular Function, Myocardial, Redox State, and High Energy Phosphate Profile. A Phosphorous-31 Nuclear Magnetic Resonance Study," *J. Surg. Res.*, 35:332-339 (1983).

Venkatachalam, M., J. Kriesberg, J. Stein, M. Lifschitz, "Salvage of Ischemic Cells by Impermeant Solute and Adenosinetriphosphate," *Lab. Investig.*, 49(1):1-3 (1983).

Zang, D., et al,, "The Distribution of Liposome-Encapsulated ATP in Experimental Ischemic Myocardium", Chemical Abstracts, vol. 109, No. 11, 85657M, Sep. 12, 1988.

\* cited by examiner

WOUND HEALING COMPOSITIONS AND METHODS OF USE

RELATED APPLICATIONS

This application is a continuation of U.S. application Ser. No. 10/397,048, A DIRECT CELLULAR ENERGY DELIVERY SYSTEM, to William D. Ehringer and Sufan Chien, filed Mar. 25, 2003, which claims priority to U.S. provisional application Ser. No. 60/380,762, FUSOGENIC LIPID VESICLES, to William D. Ehringer and Sufan Chien, filed May 14, 2002, both of which are incorporated herein by reference in their entireties.

BACKGROUND

ATP is the fuel that powers all cells-animal, plants, bacteria, fungi, etc. Such as a car without gas, humans and other creatures with an empty ATP "tank" do not go. In fact, they die. The energy derived from the breakdown of nutrients is ultimately conserved in the high energy phosphate bonds of ATP. When these bonds are broken, they provide accessible energy to cells, tissues, organs and organ systems. Cells constantly synthesize and metabolize ATP. ATP can be produced either aerobically through oxidative phosphorylation, with oxygen as the terminal electron acceptor and yielding carbon dioxide ($CO_2$) and water as by-products, or anaerobically during glycolysis. While glycolysis can provide energy to cells, the supply is limited because the cellular environment becomes acidic, injuring the cell and inhibiting ATP production.

The vascular circulatory system delivers a continuous supply of energy that is derived from oxygen and nutrients. In the vasculature, a barrier of endothelial cells separates the cells being fed from the vessel lumen. To reach individual cells, oxygen and nutrients must pass through the endothelial lining into the interstitial space to deliver oxygen and nutrients. This oxygen supply can be cut off or reduced as a result of disease or trauma.

Supplying energy to cells would be preferably accomplished by direct administration of ATP; however, cells take up exogenous ATP poorly because they lack ATP receptors or channels. Furthermore, cell plasma membranes are hydrophobic, while ATP is hydrophilic, preventing the ATP from passing through. Introducing ATP into the blood stream is ineffective because ATP cannot cross the endothelial barrier, and ATP is prone to hydrolysis. Attempts to use liposomes to deliver ATP have been largely unsuccessful and inefficient (Arakawa et al. 1998, Puisieux et al. 1994). For example, Puisieux et al. constructed phosphatidyl choline, cholesterol and phosphatidyl serine lipid vesicles that encapsulated ATP, then incubated the vesicles with sperm cells, liver and brain tissue. Although some uptake was observed, controlled delivery matching metabolic demand for ATP was not achieved. When administered in the blood stream, liposomes are usually unable to breach the endothelial cell barrier; in addition, they usually do not have high rates of fusion with cellular membranes, a necessary event for the vesicle to deliver its ATP payload into the cells.

Animal cell plasma membranes contain four major phospholipids that represent greater than half of the total lipid: phosphatidylcholine, phosphatidylethanolamine, phosphatidylserine and sphingomyelin. Phosphatidylcholine and sphingomyelin are found mostly in the outer leaflet, while phosphatidylethanolamine and phosphatidylserine are found principally in the inner leaflet. The predominance of the negatively-charged phosphatidylserine and phosphatidylinositol in the outer leaflet results in a net negative charge on the cells surface. Plasma membranes help maintain cellular integrity and are selectively permeable. While some molecules are able to diffuse through membranes, most, including ATP, require other means to enter, such as transport proteins or channels.

SUMMARY

In a first aspect, the present invention is a wound-healing composition, comprising a wound-treating component and vesicles. The vesicles comprise ATP and a phospholipid which is a stable vesicle former.

In a second aspect, the present invention is a wound-healing composition, comprising at least one member selected from the group consisting of becaplermin, an antiseptic, an antibiotic, and an anesthetic and vesicles. The vesicles comprise: a phospholipid which is a stable vesicle former; a polar lipid which is not a stable vesicle former; and ATP.

Definitions

"Alkyl" (or alkyl-or alk-) refers to a substituted or unsubstituted, straight, branched or cyclic hydrocarbon chain, preferably containing of from 1 to 20 carbon atoms. Suitable examples of unsubstituted alkyl groups include methyl, ethyl, propyl, isopropyl, cyclopropyl, butyl, iso-butyl, tert-butyl, sec-butyl, cyclobutyl, pentyl, cyclopentyl, hexyl, cyclohexyl, and the like. "Alkylaryl" and "alkylheterocyclic" groups are alkyl groups covalently bonded to an aryl or heterocyclic group, respectively.

"Alkenyl" refers to a substituted or unsubstituted, straight, branched or cyclic, unsaturated hydrocarbon chain that contains at least one double bond, and preferably 2 to 20 carbon atoms. Exemplary unsubstituted alkenyl groups include ethenyl (or vinyl), 1-propenyl, 2-propenyl (or allyl) 1,3-butadienyl, hexenyl, pentenyl, 1,3,5-hexatrienyl, and the like. Preferred cycloalkenyl groups contain five to eight carbon atoms and at least one double bond. Examples of cycloalkenyl groups include cyclohexadienyl, cyclohexenyl, cyclopentenyl, cycloheptenyl, cyclooctenyl, cyclohexadienyl, cycloheptadienyl, cyclooctatrienyl and the like.

"Alkoxy" refers to a substituted or unsubstituted, -0- alkyl group. Exemplary alkoxy groups include methoxy, ethoxy, n-propoxy, isopropoxy, n-butoxy, t-butoxy, and the like.

"Aryl" refers to any monovalent aromatic carbocyclic or heteroaromatic group, preferably of 3 to 10 carbon atoms. The aryl group can be bicyclic (i.e., phenyl (or Ph)) or polycyclic (i.e., naphthyl) and can be unsubstituted or substituted. Preferred aryl groups include phenyl, naphthyl, furyl, thienyl, pyridyl, indolyl, quinolinyl or isoquinolinyl.

"Amino" refers to an unsubstituted or substituted-NRR' group. The amine can be primary (—NH2), secondary (—NHR) or tertiary (—NRR'), depending on the number of substituents (R or R'). Examples of substituted amino groups include methylamino, dimethylamino, ethylamino, diethylamino, 2-propylamino, 1-propylamino, di (n-propyl) amino, di (iso-propyl) amino, methyl-n-propylamino, t-butylamino, anilino, and the like.

"Heterocyclic radical" refers to a stable, saturated, partially unsaturated, or aromatic ring, preferably containing 5 to 10, more preferably 5 or 6, atoms. The ring can be substituted 1 or more times (preferably 1, 2, 3, 4 or 5 times) with a substituent. The ring can be mono-, bi-or polycyclic. The heterocyclic group consists of carbon atoms and from 1 to 3 heteroatoms independently selected from the group consisting of nitrogen, oxygen, and sulfur. The heteroatoms can be protected or unprotected. Examples of useful heterocyclic groups include substituted or unsubstituted, protected or unprotected acridine, benzathiazoline, benzimidazole, benzofuran, benzothiophene, benzthiazole, benzothiophenyl, carbazole, cinnoline, furan, imidazole, 1H-indazole, indole, isoindole, isoquinoline, isothiazole, morpholine, oxazole (i.e., 1,2,3-oxadiazole), phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, triazole (i.e., 1,2,3-triazole), and the like.

"Substituted" means that the moiety contains at least one, preferably 1–3 substituent (s). Suitable substituents include hydrogen (H) and hydroxyl (—OH), amino (—NH2), oxy (-0-), carbonyl (—CO—), thiol, alkyl, alkenyl, alkynyl, alkoxy, halo, nitrile, nitro, aryl and heterocyclic groups. These substituents can optionally be further substituted with 1–3 substituents. Examples of substituted substituents include carboxamide, alkylmercapto, alkylsulphonyl, alkylamino, dialkylamino, carboxylate, alkoxycarbonyl, alkylaryl, aralkyl, alkylheterocyclic, and the like.

DETAILED DESCRIPTION

Figure 1:
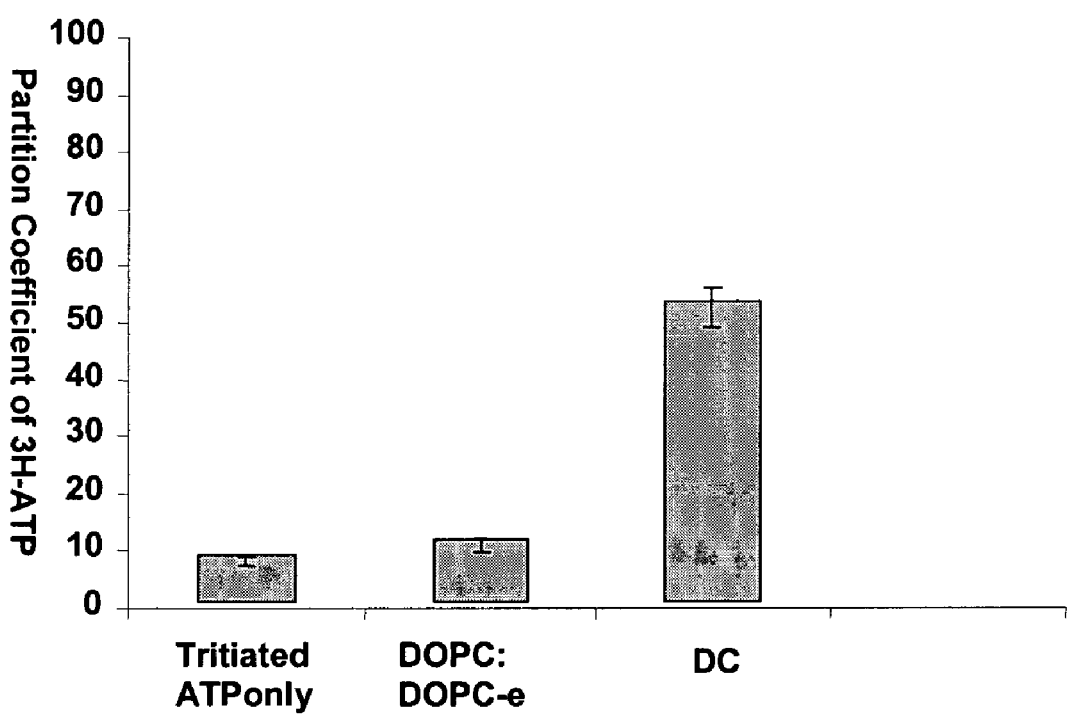
FIG. 1 shows the partition coefficient of ATP within human umbilical vein endothelial cells (HUVEC) after one hour.

The present invention makes use of the discovery that small lipid vesicles that are fusogenic with cellular bilipid membranes can encapsulate ATP and deliver the ATP directly to cells. The rate of ATP delivery is easily controlled by varying the lipid vesicle composition, as well as by other means, resulting in different fusion rates. In addition, the vesicle composition can be modulated to accommodate different modes of administration. For example, small lipid vesicles can be made such that when injected into the circulation, the vesicles fuse with endothelial cells, opening up gaps so that they can fuse efficiently with the target cells. To encourage or target fusion, other components may be added to the vesicles, such as certain polypeptides. By being loaded into a lipid vesicle, ATP is stabilized against hydrolysis.

The compositions and methods of the invention meet the requirements for effective ATP delivery to cells. Lipid vesicle membranes resemble plasma cell membranes; in addition, they are simple to make. Because they have an aqueous portion, lipid vesicles can encapsulate various solutions, including those containing ATP. Lipid vesicles can be made to fuse with cell membranes, allowing for the delivery of the lipid vesicles's contents. The methods and compositions of the invention have a large array of uses, including treating wound healing.

The following, not meant to limit the invention, is presented to aid the practitioner, although other methods, techniques, cells, reagents and approaches can be used.

Fusogenic Lipid Vesicles

Lipid vesicles resemble plasma membranes, and they can be made to fuse with cell membranes. Most liposomes and multilamellar vesicles are not readily fusogenic, mainly because the stored energy of the vesicle radius of curvature is minimal. But the small unilamellar vesicles of the present invention, which have a very tight radius of curvature, are very fusogenic. The average diameter of a small unilamellar vesicle (SUV) is 5 nm to 500 nm; preferably 10 nm to 100 nm, more preferably 20 nm to 60 nm, including 40 nm. This size allows vesicles to pass through the gaps between endothelial cells. Useful vesicles may vary greatly in size and are selected according to a specific application.

The compositions from which the vesicles of the present invention are formed contain a phospholipid which is a stable vesicle former, preferably together with another polar lipid, and optionally with one or more additional polar lipids and/or raft formers.

Polar lipids are organic molecules which have a hydrophobic end and a hydrophilic end, and contain at least six carbon atoms; they have the structure of formula (I), where X is a head group, L is a back bone group, and each Z is a fatty group. The two Z groups may be the same or different. A phospholipid is a polar lipid which has a head group of formula (II), where A and B are substituents of the head group.

The head group, X, may be any polar group, preferably a cationic, anionic or zwitterionic group, or H. More preferably X is a group of formula (II). Preferably, B is an cation, such as $Na^+$, $K^+$, or tetramethyl ammonium ion; or an alkyl group. Preferably, A is H, or an alkyl group; more preferably A is an alkyl group substituted with an amine; most preferably A is a group of formula (III), (IV), (V), (V) or (VII). It should be noted that throughout the specification, the formulas may show the structures in protonated form, but that they also include the unprotonated form (and visa versa); which form is present in any composition will depend on the exact pH of the composition, and the presence of water and/or appropriate counter ions.

The back bone group, L, is an alkyl further missing two hydrogen atoms (to give a total of three open attachment points), preferably an alkoxy, or amino substituted alkyl. Most preferably, L is a group of formula (VIII), (IX) or (X).

The fatty groups, Z, may be the same or different, and are H, an E group, or the structure of formula (XI), where E is an alkyl or alkenyl. Preferably, E is an unsubstituted straight chain alkyl or alkenyl, with 6–26 carbon atoms; more preferably E is a group of formula (XII), (XIII), (XIV), (XV), or (XVI). If one of the fatty groups is H, then the other must be different. If double bands are present, then cis configuration is preferable.

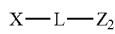
(I)

(II)

-continued

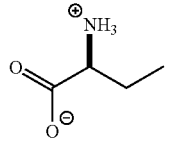 (III)

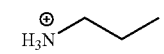 (IV)

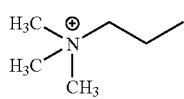 (V)

(VI)

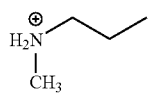 (VII)

(VIII)

(IX)

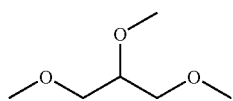 (X)

 (XI)

(XII)

(XIII)

(XIV)

(XV)

(XVI)

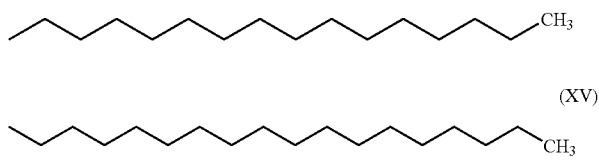

A phospholipid (or polar lipid) which is a stable vesicle former is a phospholipid (or polar lipid) that will form vesicles, at least 50% of which persist for at least one hour, when prepared as follows: the phospholipid is dissolved in chloroform and placed in glass test tube. Solvent is removed by evaporation under a steady stream of nitrogen, followed by air removal by subjecting the sample to vacuum for twelve hours. The dried lipid material is then re-hydrated in 10 mM $Na_2HPO_4$, for 60 minutes at a temperature above the lipid phase transition temperature; the desired final concentration is 25 mg/ml. The lipid mixture is then agitated by sonication with a microtip 450 watt sonicator used at a 40% duty cycle.

Preferably, in addition to the phospholipid which is a stable vesicle former, at least one other polar lipid is included, more preferably one or more polar lipids which are not stable vesicle formers.

A raft former is a compound which will sit within the lipid layer of a vesicle when the vesicle is in an aqueous solution, and will form or cause formation of discrete regions within the vesicle wall (also known as rafts). These discrete regions tend to destabilize the vesicle, increasing its fusogenicity. Examples of raft formers are cholesterol (formula XXIV), sphingomyelin, and proteins and polypeptides know to be membrane bound. Fusogenicity may also be enhanced by selecting polar lipids, which will result in a surface charge on the vesicle, which is the opposite of the charge of the Gouey-Chapman layer of the target cells (typically the Gouey-Chapman layer is positively charged).

Examples of polar lipids for use in the present invention include 1,2-dioleoyl-sn-glycero-3-phosphocholine (DOPC) (formula XVII; a stable vesicle former), 1-palmitoyl-2-oleoyl-sn-glycero-3-phosphate (POPA) (shown as the monosodium salt in formula XVIII), 1,2-dioleoyl-sn-glycero-3-ethylphosphocholine (DOPC-e) (shown as the chloride salt in formula XIX), 1,2-dioleoyl-sn-glycero-3-phosphoethanolamine (DOPE) (formula XX), 1,2-dioleoyl-sn-glycero-3-[phospho-1-serine] (DOPS) (shown as the sodium salt in formula XXI), 1-palmitoyl-2-docosahexaenoyl-sn-glycero-3-phosphocholine (formula XXII; a stable vesicle former), a typical sphingomyelin (formula XXIII; cholesterol will form rafts when added to a vesicle formed from a mixture this sphingomyelin and DOPC), 1,2-dimyristoyl-sn-glycerol (formula XXV), and 1-palmitoyl-2-hydroxy-sn-glycero-3-phosphocholine (XXVI). Other polar lipids useful for the practice of the present invention include phosphatidyl serine (PS), phosphatidyl glycerol (PG), mixed chain phosphatidyl choline (MPC), phosphatidyl ethanol (PE), and phospholipids containing decosahexaenoic acids. Cit-DOPC and cit-DOPC-e are especially useful. Phosphatidylcholines, including those having a docosahexaenoic acid in the sn-1 and sn-2 positions (DHPC) may be used. Other diunsaturated lipids, such as diarachidonylphosphatidylcholine (for example 20:4 DOPC:DArPC), dilinolenoylphosphatidylcholine (for example 18:3 DOPC:DLnPC) are also useful. For example, DOPC may be mixed with increasing amounts of DLnPC, DArPC and DHPC during SUV preparation. Useful ratios include (DOPC:DLnPC, DArPC or DHPC) range from 1–1000:1, such as 25–500:1, including 1:1, 25:1, 50:1, 100:1, 500:1, and 1000:1. Combinations of phospholipids having large mean molecular areas can also be used, such as DOPC:DLnPC:DHPC. Diacylglyercol, a non-lamellar phase lipid, can also be mixed with DOPC. In addition, one can use polyethylene glycol (PEG) with weights of 20 repeats up to 4000 repeats.

Preferably, the ratio of the stable vesicle former phospholipid to the polar lipid which is not a stable vesicle former is 1:1 to 500:1, more preferably 10:1 to 100:1 (for example, 50:1). Examples include: DOPC/DOPC-e (1:1); DOPC/POPA (50:1) and DOPC/POPA (1:1).

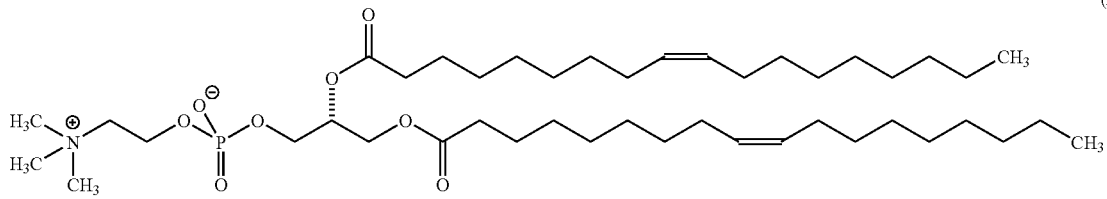
(XVII)

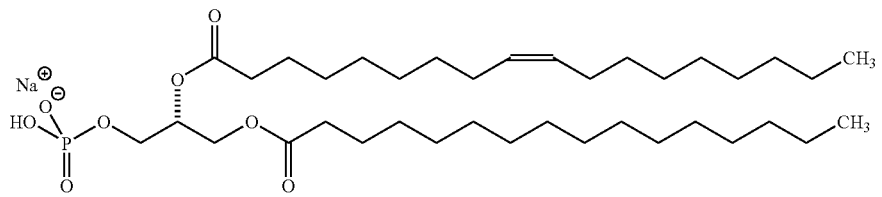
(XVIII)

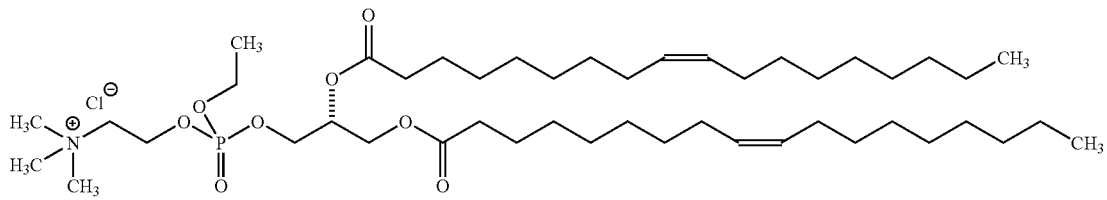
(XIX)

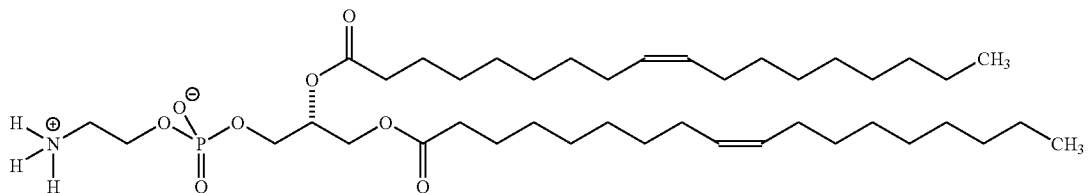
(XX)

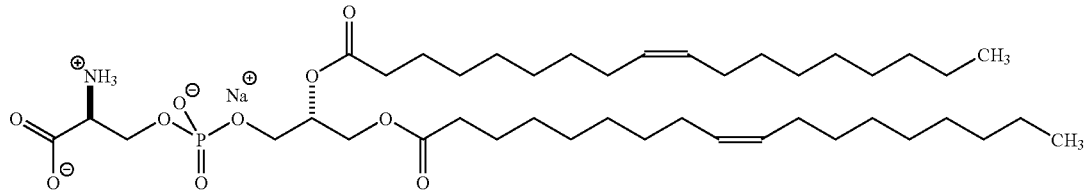
(XXI)

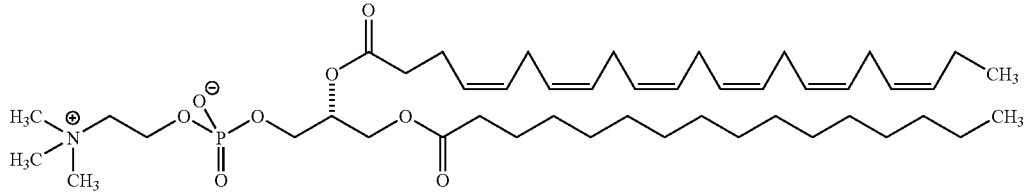
(XXII)

-continued

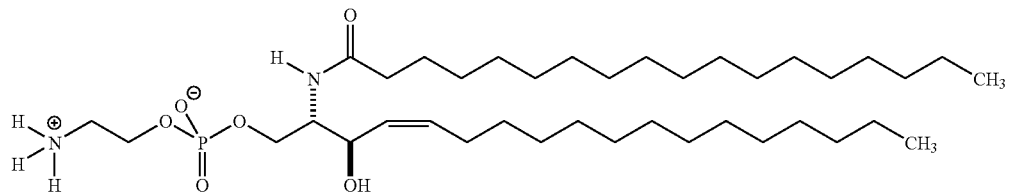
(XXIII)

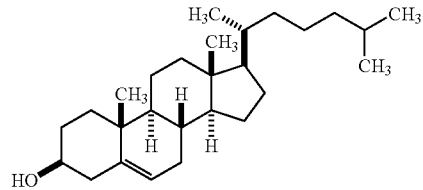
(XXIV)

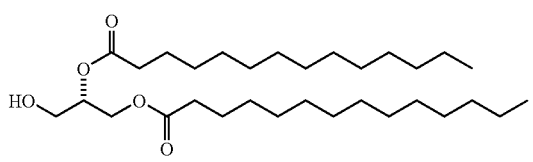
(XXV)

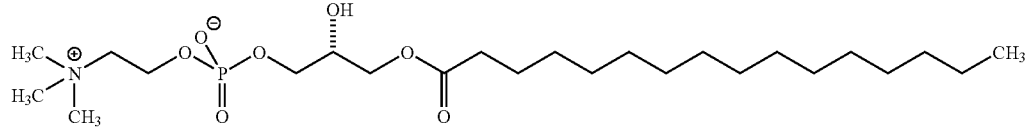
(XXVI)

Lipid Vesicle Construction

To construct lipid vesicles, lipids are dissolved in chloroform or other appropriate organic solvent and placed in a vessel, such as glass test tube. Solvent is removed by evaporation under a steady stream of nitrogen or other neutral gas, followed by air removal, such as subjecting the sample to a vacuum for 0.1 to 48 hours, such as 1, 2, 3, 4, 5, 6, 7, 8, 9, 10, 11, 12, 15, 20, 24, 25, 30, 36, 40, 42 or 48 hours. Twelve hours usually suffices. The dried lipid material is then re-hydrated in an appropriate buffer, such as Hank's Balanced Salt Solution (HBSS) or 10 mM $Na_2HPO_4$, for 30–60 minutes at a temperature above the lipid phase transition temperature; the desired final concentration is usually approximately 1 to 30 mg/ml, typically around 25 mg/ml. The lipid mixture is then agitated. For example, sonication can be used; such as a microtip 450 watt sonicator used at a 40% duty cycle to create SUVs. The length of time of sonication depends on the amount of lipid material; in any case, sonication is stopped when no further decreases in percent transmission are observed or the correct vesicle size is achieved by analysis using a particle size analyzer. Lipids can be analyzed by UV spectroscopy and thin layer chromatography (TLC) to assess the extent of oxidation, if desired.

Other solutions may be used when rehydrating the dried lipids. These include those buffered with N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glyclclycine, N-2-hydroxyehtylpiperazine-N'-2-ethanesulfonic acid (HEPES), 3-(N-morpholino) propane sulfonic acid (MOPS), Piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl) methyl-2-aminoethanesulfonic acid (TES), N-tris (hydroxymethyl)methyl-glycine (Tricine), and tris (hydroxymethyl)-aminomethane (Tris). Other examples of suitable solutions include salt solutions, such as Alseverr's Solution, Dulbecco's Phosphate Buffered Saline (DPBS), Earle's Balanced Salt Solution, Gey's Balanced Salt Solution (GBSS), Puck's Saline A, Tyrode's Salt Solution, St. Thomas Solution and University of Wisconsin Solution.

Other components may be incorporated into SUVs to manipulate their fusion rates. For example, polypeptides that are involved in membrane fusion, such as fertilin, soluble N-ethylmaleimide-sensitive factor attachment protein receptors (SNAREs), SM (sec1/munc18) polypeptides (such as mammalian isoforms of Vps33p, Sly1p and Vps45p; (Jahn and Sudhof 1999)) and viral envelope fusion proteins, such as those from Human Immunodeficiency Virus (HIV; e.g., gp41), Semiliki Forest virus, and Influenza). The mammalian SNARE family includes the syntaxins (1A, 1B, 1C; 2 (and splicing variants); 3, 3A, 3B, 3C, 3D; 4; 5, 5A, 5B, 6, 7, 8, 10, 11, 12, 13 (may be identical to 12); 16 (A, B, C); and 17), Hsyn 16, rbet1, GS15, GOS32, GOS28, Membrin, the SNAPs (25, 25a, 25b; 23, 23A, 23B; 29), vti1b, Synaptobrevins (1 and splicing variants; 2), Cellubrevin, VAMP4, VAMP5/6, Ti-VAMP, Endobrevin, Tomosyn and msec22b (Jahn and Sudhof 1999). Other amphiphilic peptides that destabilize membranes, even if their primary function is not to mediate membrane fusion, can also be used to promote fusion, such as annexins (Jahn and Sudhof 1999).

ATP Encapsulation

Typically, the magnesium salt of ATP is added at the time of lipid re-hydration. ATP concentration may vary and will depend on the application. Concentrations of ATP that are preferably used include 0.01 mM to 200 mM, preferably 0.1 mM, 1 mM, 2.5 mM, 5 mM, 7.5 mM, 10 mM, 25 mM, and 50 mM, and more preferably, 0.1 mM, 1 mM, 10 mM. The buffer containing the ATP should have a low protein content to decrease the chance of non-specific absorption of the lipid material. SUVs that contain ATP are referred to as ATP-SUV for convenience.

Encapsulation of ATP by SUVs can easily be assessed. For example, labeled ATP molecules (such that the label does not interfere with vesicle formation), such as radiolabeled ATP, preferably tritiated ATP is used. Radiolabels include $^{32}P$, and $^3H$ and are added when the lipids are re-hydrated after drying, prior to agitation. The solution is applied to a Sephadex G-25 column (or other suitable matrix) to remove non-encapsulated ATP. The effluent from the column is collected and assayed for the presence of vesicles. SUVs are usually eluted in the earliest fractions. Percent encapsulation is determined by quantifying the radioactivity in the vesicle and supernatant fractions, and determining the proportion of encapsulated ATP and multiplying by 100. Preferable encapsulation percentages range from approximately 1% to 10%.

Molecules other than ATP may be delivered to cells using SUVs, such as organic and inorganic molecules, including pharmaceuticals, polypeptides, nucleic acids and antibodies that interact with intracellular antigens.

Assay for Measuring SUV Fusogenicity

The fusion rate is a measure of the number of lipid vesicles that fuse with the HUVEC cells in a well/second (about $10^6$ cells), the assays has the following steps:

(1) HUVEC cells (American Type Culture Collection (ATCC); Manassus, Va. or BioWhittaker; MD) are cultured;

(2) SUVs are prepared and loaded with a fluorescent probe, such as carboxyfluorescein;

(3) the SUVs are contacted to the cells to allow for fusion;

(4) at a selected time, any residual SUVs are removed; and (5) fluorescence is measured.

The presence and intensity of a fluorescent signal after removing the SUVs indicates the ability of the SUVs to fuse with the cell membranes and deliver the contents.

Human umbilical vein endothelial cells (HUVECs) is given as an example. The cells are grown to confluence on a standard 12-well culture dishes (for example, from COS-TAR; the number of cells is approximately $10^6$) in endothelial cell growth medium (EGM). The HUVECs are then washed 3 times with a buffer, such as HBSS. Prepared lipid vesicles (such as DOPC/DOPC-e (1:1); DOPC/POPA (50:1), DOPC/POPA (1:1), PS, PG, MPC, PE, cit-DOPC and cit-DOPCe), are loaded with 1 mM carboxyfluorescein. The vesicles are incubated with the cells for 120 minutes, assaying fluorescence at each 5 minute increment, at 37° C., 95% air/5% $CO_2$, after which time residual vesicles are removed by washing the cells with buffer. If negatively charged lipid vesicles are used, calcium (final concentration 0.1–10 mM) is added at the fusion step.

Cells are removed from the dish by treating with trypsin. Fluorescence is measured (excitation at 495 nm and emission of 520 nm) using a luminescence spectrophotometer or other suitable device.

The rate of fusion for ATP-SUV compositions is approximately 20 vesicle fusions/second to $8.0 \times 10^{11}$ vesicle fusions/second, including 500 to $1 \times 10^8$ vesicles fusions; 750,000 to $50 \times 10^7$ vesicle fusion/second; $5 \times 10^6$ to $1 \times 10^7$ vesicle fusions/second; including $1 \times 10^6$ to $8 \times 10^8$ vesicle fusions/second; $1 \times 10^7$ to $5 \times 10^8$ vesicle fusions/second; and $5 \times 10^7$ to $1 \times 10^8$ vesicle fusions/second. Examples of fusion rates are at least 100, 1000, $10^4$, $10^5$, $10^6$, $10^7$, $10^8$, $10^9$, $10^{10}$, and $10^{11}$ vesicle fusions/second. Some of these values were obtained experimentally at 37° C. using mixtures of DOPC and DOPC/DOPC-e and DOPC/POPA, with and without calcium, and using human endothelial cells.

Because the lipid composition of plasma membranes varies by cell type, the choice of cells for use in the assay is carefully considered, and should match as best the target cell type(s). For example, liver cell plasma membranes consist of about 7% phosphatidylethanolamine, while red blood cell plasma membranes contain 18% (Alberts et al. 2002). Primary culture cells, as well as cell lines (available from the American Type Tissue Collection (ATCC); Manassus, Va.) are useful, although primary cultures are preferred because of the likelihood that the plasma membrane lipid composition is altered in transformed cells. Cell types include pancreas, intestinal, immune system, neuronal (including those of the brain, eye, nose and ear), lung, heart, blood, circulatory (lymph and blood), bone, cartilage, reproductive, glandular, enamel, adipose, skin, and hepatic. Cell lines include those derived from these tissues, such as Madin-Darby canine kidney (MDCK), Chinese hamster ovary (CHO), HeLa, etc. Cells may be from other organisms, such as plants, fungi (including yeasts), and bacteria. Examples of fusion rates with these other cell types include at least 100, 1000, $10^4$, $10^5$, $10^6$, $10^7$, $10^8$, $10^9$, $10^{10}$, and $10^{11}$ vesicle fusions/second. Unless otherwise specified, fusion rates are with respects to HUVECs under the conditions specified above. Fusion rates with respects to other cell types is for about $10^6$ cell, with a buffer, such as HBSS, and the vesicles are incubated with the cells for 120 minutes at 37° C., 95% air/5% $CO_2$, after which time residual vesicles are removed by washing the cells with buffer.

Altering Fusion Rates

Creating Dissimilar Lipid Phases

Plasma membranes contain lipid domains or rafts that are enriched in a particular lipid species. At the boundary of such a membrane raft are regions of dissimilar lipid species. These regions have the potential for instability, effecting how the membrane interacts with other membranes. Several phospholipids are known to increase lipid raft formation, including mixtures of phosphatidylcholines, sphingomyelin, and cholesterol. For example, DOPC, 18:0 sphingomyelin, and cholesterol are mixed in a 1:1:1 ratio during SUV preparation. Cholesterol preferentially partitions in the sphingomyelin phase, creating regions that are rich in DOPC and poor in cholesterol, and regions that are rich in sphingomyelin and rich in cholesterol.

Changing the physical parameters of fusion, temperature, concentration, ionic strength, and fusion period, can be used to affect fusion rates. By altering temperature, the free energy (G) of the system is altered, leading to different rates of fusion. Increasing lipid vesicle concentration also affects membrane fusion rates, especially at very high concentrations. The fusion period (length of fusion) and the number of fusion periods also affect the rate of delivery of the encapsulated contents of SUVs.

Concentration on Vesicle Fusion

While intuitive that increased concentration leads to increased SUV content delivery, the rate of membrane fusion is not linear. Once SUV lipids occupy all of the available plasma membrane surface, further fusion is limited. The extent of fusion with the plasma membrane affects membrane volume and properties, such as ion permeability and lipid organization. Therefore, when administering SUVs, SUV concentration must be controlled so that the target cells are effectively treated.

Administration

Pharmaceutical Compositions

In many cases, ATP-SUV may be delivered as a simple composition comprising the ATP-SUV and the buffer with which it was made. However, other products may be added, if desired, such as those traditionally used as carriers in pharmaceutical compositions.

A "pharmaceutically acceptable carrier" includes any and all solvents, dispersion media, coatings, antibacterial and antifungal agents, isotonic and absorption delaying agents, and the like, compatible with pharmaceutical administration (Remington 2000). Preferred examples of such carriers or diluents include water, saline, Ringer's solutions and dextrose solution. Supplementary active compounds can also be incorporated into the compositions.

General Considerations

A pharmaceutical composition of the invention is formulated to be compatible with its intended route of administration, including subcutaneous, oral, inhalation, transdermal, transmucosal, and rectal administration. Solutions and suspensions used for parenteral, intradermal or subcutaneous application can include a sterile diluent, such as water for injection, saline solution, polyethylene glycols, glycerine, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

If negatively charged lipid vesicles are used in the ATP-SUV compositions, calcium is included such that the final concentration at the site of fusion is preferably 0.1 mM-10 mM; including 0.1, 1, 2, 3, 4, 5, 6, 7, 8, 9 or 10 mM.

The ATP in ATP-SUVs is usually in equilibrium with the ATP in any solution surrounding the ATP-SUVs; typically only 1–10% of the total ATP is within the ATP-SUVs. The remaining ATP may bind to receptors, such as the purinoreceptor P2y, causing ions to flow out of the cells, and interfering with ion balance and homeostasis. Although the cells can usually reestablish ion balance and homeostasis, this consumes additional ATP. Therefore, particularly with tissue for which immediate restoration of function is desirable (for example, during organ transplantation, or limb reattachment), including in the composition one or more purinoreceptor P2y antagonists, is advantageous. The purinoreceptor P2y antagonists is preferably added to the composition after forming the vesicles, or just prior to administration, since the antagonists do not need to be within the SUVs. Examples of purinoreceptor P2y antagonists include pyridoxal 5-phoshpate, vitamin B6 (pyridoxal-5-phosphoric acid), and Reactive Blue 2(1-amino-4-[[4-[[4-chloro-6-[[3(or 4)-sulfophenyl]amino]-1,3,5-triazin-2-yl]amino]-3-sulfophenyl]amino-9,10-dihydro-9,10-dioxo-2-anthracenesulfonic acid), and combinations thereof. The purinoreceptor P2y antagonists may preferably be used in a concentration of 0.1–250 micromoles/L, more preferably 1–100 micromoles/L.

Transmucosal or Transdermal

Administration can be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams. Suppositories (e.g., with bases such as cocoa butter and other glycerides) or retention enemas for rectal delivery may also be prepared.

Carriers

In one embodiment, the active compounds are prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art.

Dosage

Dosage is dictated by, and directly depends on, the unique characteristics of ATP-SUV which varies with different SUV lipid compositions, the particular desired therapeutic effect, and the route of administration. The specific dose level and frequency for any particular patient or application may be varied. Factors that should be considered, including (1) the temperature at which administration is made and at which fusion is permitted; (2) the ionic environment of the administration site and the ionic strength of the ATP-SUV composition; and (3) the length of time that fusion is permitted. Controlling these factors helps to control the extent to which the encapsulated substances, including ATP, are delivered.

When administering SUVs, SUV concentration is controlled to effectively treat the target cells while not inhibiting their function by saturating the plasma membranes with SUV lipids. Preferable concentrations of SUV, depending on lipid composition, target cell dispersion and volume to be administered may be 0.5 mg/ml–100 mg/ml, such as 0.5 mg/ml, 1 mg/ml, 5 mg/ml, 10 mg/ml, 20 mg/ml, 30 mg/ml, 40 mg/ml, 50 mg/ml, 60 mg/ml, 70 mg/ml, 80 mg/ml, 90 mg/ml and 100 mg/ml.

Vesicle fusion occurring via electrostatic interactions is significantly affected by changes in calcium and/or magnesium concentrations, and to a lesser extent, changes in sodium and/or potassium concentrations. Modulating these ion concentrations either in the compositions used to administer ATP-SUV or in compositions administered to a target site before or after ATP-SUV administration, affect dosage considerations. Preferably, ion concentrations of 0.01 nM to 1 mM, including 0.11 nM, 1 nM, 10 nM, 100 nM, 1000 nM, 10 micromole/L, and 100 micromoles/L are used. Combinations of these and other ions may also be used.

ATP-SUV for Wounds

Because blood flow to wounds is diminished, less oxygen is available to the cells in and around the wound. The decrease in oxygen delivery results in a decrease in ATP production, which slows many cellular events necessary for wound healing, including protein and nucleic acid synthesis, ion channel function, signal transduction, and locomotion.

ATP-SUV is applied to the wound as necessitated by the extent of healing or the ATP consumption of the wound. For example, to provide the border cells of the wound sufficient ATP to accelerate wound closure, ATP-SUV may be applied preferably 1–12 times per day, such as 1, 2, 3, 4, 5, 6, 7, 8, 9, 10, 11 or 12 times/day. Preferably, the ATP-SUV is placed directly over the wound in a specially designed applicator which keeps the water-based ATP-SUV in direct contact with the wound border cells. Alternatively, the ATP-SUV may be applied topically as a cream or other topical pharmaceutical composition.

ATP-SUV may also be combined with healing compositions already available to further enhance healing. For example, ATP-SUV can be combined with becaplermin, as found in Regranex®. Other wound-treating components besides becaplermin include antiseptics, antibiotics, and anesthetics. The term "wound-treating component" does not include SUVs.

EXAMPLES

The following examples are provided to illustrate the invention. Those skilled in the art can readily make insignificant variations in the compositions and methods of this invention. The examples are not meant to limit the invention in any way.

Example 1

Construction of Lipid Vesicles

Vesicles were constructed from 1,2-dioleoyl-sn-glycero-3-phosphocholine (DOPC); 1,2-dioleoly-sn-glycero-3-ethylphosphocholine (DOPC-e) and 1-palmitoyl-2-oleoyl-sn-glycero-3-phosphate (POPA) lipids. (all from Avanti Polar Lipids; Alabaster, Ala.). The lipids were used without further purification. After dissolving the lipids in chloroform and placed in a glass test tube, the chloroform was removed by evaporation under a steady stream of nitrogen gas, followed by overnight vacuum pumping. The dried lipid material was re-hydrated in HBSS experimental buffer (Sigma; St. Louis, Mo.) above its phase transition temperature (25° C.) for 30 minutes. Two glass beads were added to the buffer/lipid mixture, and the suspension vortexed for five minutes to create multilamellar vesicles. The milky solutions was then sonicated using a microtip Branson Sonifier 450, with the microtip placed in the test tube. The vesicles were then sonicated for five minutes at level 5 with a 40% duty cycle to create small unilamellar vesicles (SUVs).

Example 2

Encapsulation of ATP

To demonstrate incorporation of ATP into the vesicles of Example 1, 30 µCi of $^3$H-ATP (Amersham; Arlington Heights, Ill.) was added to the experimental buffer prior to creating the multilamellar vesicles. The suspension was passed over a Sephadex G-25 (Sigma) column (1 cm×40 cm) to remove the non-encapsulated ATP. The vesicles were collected in the first 50 ml of the effluent. The percent encapsulation was determined by measuring the radioactivity contain within the vesicles and in the supernatant by liquid scintillation counting. Vesicles comprising DOPC, DOPC:DOPC-e (1:1), DOPC:POPA (50:1) and DOPC:POPA (1:1) all gave approximately the same percent encapsulation of ATP, varying between 1 to 2.5% of the original amount of ATP in solution.

Example 3

Rate of Fusion of Vesicles to HUVEC and Release of Encapsulated Contents into the Cytoplasm To determine the fusogenic rate of SUVs, SUVs were loaded with a fluorescent probe, presented to cells in vitro, washed, and then analyzed for cellular fluorescence.

Human umbilical vein endothelial cells (HUVEC) were purchased from BioWhitaker (Walkersville, Md.) at passage 1 and cultured until passage 8, after which they were no longer used. HUVEC were grown endothelial cell growth medium (EGM; BioWhitaker) to confluence on 12-well culture dishes in EGM medium. The HUVEC were then washed 3 times with HBSS. Lipid vesicles were made as in Example 1, but 1 mM carboxyfluorescein was loaded into the vesicles. The vesicles were then incubated with the cells for either 5, 10, 30, 45, 60, 90, 120 or 240 minutes at 37° C. in a humidified $CO_2$ incubator, after which the vesicles were washed from the cells, and the cells removed from the dish by gentle treatment with trypsin. The fluorescence of carboxyfluorescein in the HUVEC was measured using a Perkin-Elmer LS5OB Luminescence Spectrophotometer (Wellesly, Mass.), using an excitation of 495 nm and emission of 520 nm. In some experiments, cells were not trypsinized, and photomicrographs of the cells were taken in order to demonstrate the homogeneity of the fusion event. The range of fluorescent units (FUs) for this experiment was 0 to 450 units. The rate of fusion highly depended on the lipid composition of the SUVs. DOPC showed little or no fusion at all for the first 30 minutes, after which the fusion rate became logarithmic, reaching approximately 350 FUs. In contrast, DOPC:DOPC-e (1:1) gave a much faster initial rate of fusion and a slower final rate of fusion (approximately 35 FUs at 5 minutes; approximately 100 FUs at 120 minutes). The fastest rate of fusion was found using DOPC:POPA (1:1), which showed significant delivery of ATP within 5 minutes. As designed, the fusion rate of the three vesicles can be characterized as fast, medium and slow.

One issue which was resolved was whether the vesicles were actually fusing with the cells or simply aggregating on the cell surface. To examine this, HUVEC exposed to lipid vesicles and not removed from the culture wells were examined for the distribution of fluorescence by fluorescent microscopy. Cells exposed to all three compositions showed diffuse fluorescence throughout the cells after 5 minutes rather than punctate fluorescence, which would have suggested that lysosomes were sequestering the vesicles, thereby preventing cellular access to the carboxyfluorescein. Alternatively, the vesicles were aggregating on the cell surface. These results demonstrate that lipid vesicles fused to the cells and released the encapsulated contents within the cytoplasm rather than aggregating on the cell surface or being sequestered by lysosomes.

To determine if ATP is also introduced into cells like carboxyfluorescein, vesicle fusion and release of ATP into HUVEC was followed using the $^3$H-ATP-containing vesicles of Example 2. The vesicles were incubated with HUVEC for either 5, 10, 15, 30, 45, 60, 90, 120, or 240 minutes. The result shown in FIG. 1 is the partition coefficient of ATP inside the cells after 1 hour. DOPC/POPA gave the largest percent incorporation at this distant time period, followed by DOPC/DOPC-e, then $^3$H-ATP only, without vesicles. When the cells were washed repeatedly there was a significant change in the radioactivity of the cells. DOPC showed a slight but significant decrease in radioactivity; DOPC/DOPC-e showed no decrease in radioactivity after repeated washes, while free $^3$H-ATP showed a complete loss of radioactivity, confirming the observation that free ATP is unable to penetrate the cell membrane. These data, taken together with the fusion data, indicate that DOPC vesicles are being endocytosed, DOPC:DOPC-e vesicles are fusing, and free ATP does not enter cells. DOPC:POPA vesicles also could not be washed away, indicating that they also were fusing with cells and delivering the encapsulated contents into the cytoplasm.

Example 4

ATP-SUV Accelerates Wound Healing

Superficial wounds (approximately 80 $mm^2$ circles) were inflicted to the integument on nude mice at the upper cranial area. ATP-SUV was then applied to the wound twice daily to provide the border cells of the wound with ATP. The ATP-SUV was placed directly over the wound in a specially designed applicator which kept the water-based ATP-SUV in direct contact with the wound.

Figure 2:
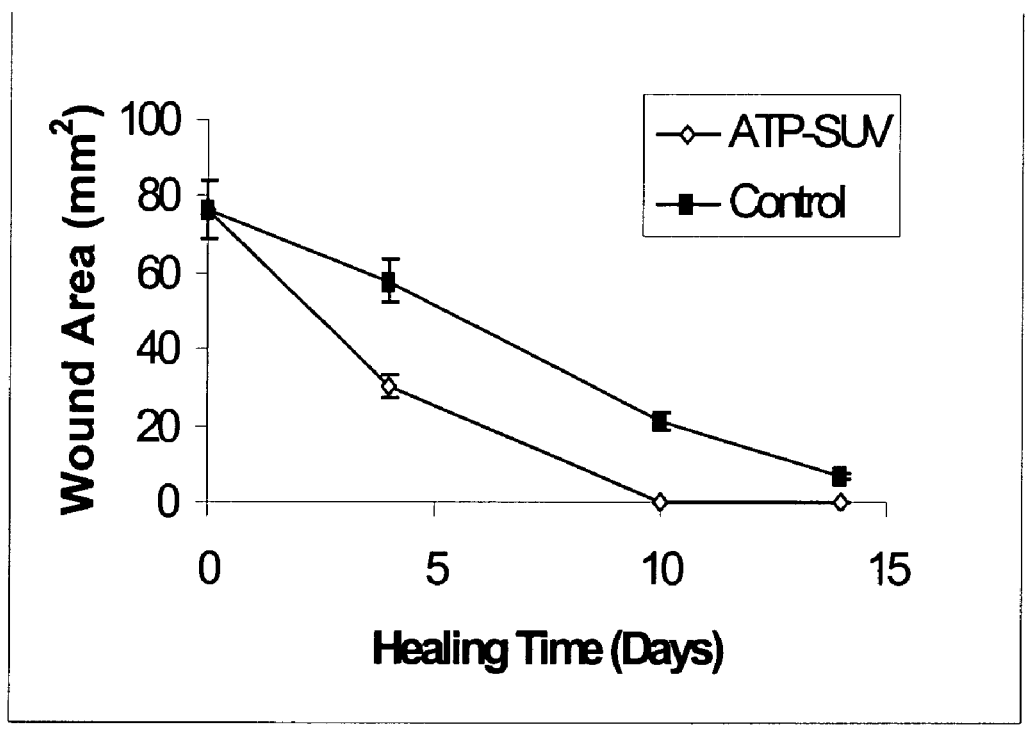
FIG. 2 shows the effects of the compositions of the invention on wound healing, in a nude mouse.

As seen in FIG. 2, wounds treated with ATP-SUV compared to those treated with control substances healed more quickly. The curve for ATP-SUV-treated wounds, plotting wound area against healing time, demonstrates a logarithmic curve, while controls showed a more linear rate of healing.

On Day 4, a difference of approximately 30 mm² is observed between the ATP-SUV treatment (≈30 mm²; less than half of the original wound area) and the control treatment (≈60 mm²); while at day 10, the wound area is virtual gone in ATP-SUV treated wounds, but not in control treated wounds (≈25 mm²). Qualitatively, Day 4 of VitalSol treated wounds resembled those of Day 10 in controls; while Day 10 mimicked the controls at Day 17. The wound was healed by Day 17 in wounds treated with ATP-SUV, while controls on this day were not yet completely healed.

REFERENCES

Alberts B, Johnson M A, Lewis J, Raff M, Roberts K, Walter P, (2002) Molecular Biology of the Cell. Garland Science, New York.
Ainscow, E. K., and Brand, M. D. (1999) Top-down control analysis of ATP turnover, glycolysis and oxidative phosphorylation in rat hepatocytes. Eur. J. Biochem. 263: 671–685.
Arakawa A, Ishiguro S, Ohki K, Tamai M. (1998) Preparation of liposome-encapsulating adenosine triphosphate. *Tohoku J Exp Med* 184: 39–47.
Brand, M. D. (1995). Measurement of mitochondrial proton motive force. In Bioenergetics, a Practical Approach/ Brown, G. C., and Cooper, C. E., eds. Oxford University Press, Oxford. 39–62.
Jahn R, Sudhof T C. (1999) Membrane fusion and exocytosis. *Annu Rev Biochem* 68: 863–911.
Puisieux F, Fattal E, Lahiani M, Auger J, Jouannet P, Couvreur P, Delattre J. (1994) Liposomes, an interesting tool to deliver a bioenergetic substrate (ATP), in vitro and in vivo studies. *J Drug Target* 2: 443–448.
Remington: the science and practice of pharmacy (2000) Alfonso R. Gennaro, chairman of the editorial board and editor. Edition: 20th ed. Lippincott Williams & Wilkins, Baltimore, Md.

The invention claimed is:

1. A wound-healing composition, comprising:
a wound-treating component; and
fusogenic vesicles,
wherein the vesicles comprise:
a phospholipid which is a stable vesicle former, wherein the phospholipid is a phosphatidylcholine;
at least one unstable vesicle forming member, wherein the unstable vesicle forming member is PEG or polar lipid having the structure of formula (I)

X-L-Z₂ (I)

wherein X is H or a head group comprising a polar group selected from the group consisting of formulas (III), (IV), (V), (VI), and (VII)

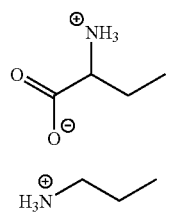

(III)

(IV)

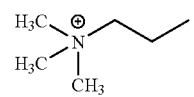

(V)

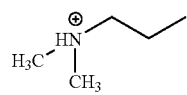

(VI)

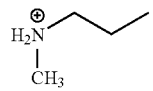

(VII)

L is an alkyl further missing two hydrogen atoms, and each Z is independently H, E, or the structure of formula (XI),

(XI)

wherein E is an alkyl or alkenyl, and when one Z is H, the other Z is not H;
and ATP at a concentration of 1 mM to 50 mM,
wherein the vesicles have a ratio of the stable vesicle former to the unstable vesicle forming member of 1:1 to 500:1 and a fusion rate of at least 20 vesicle fusions/second.

2. The wound-healing composition of claim 1, wherein the wound-treating component comprises at least one member selected from the group consisting of an antiseptic, an antibiotic, and an anesthetic.

3. The wound-healing composition of claim 1, wherein the wound-treating component comprises becaplermin.

4. The wound-healing composition of claim 1, wherein the at least one unstable vesicle forming member is PEG.

5. A method for promoting wound healing, comprising contacting a wound with the wound-healing composition of claim 1.

6. The method of claim 5, wherein the wound is a superficial wound.

7. The wound-healing composition of claim 1, wherein the at least one unstable vesicle forming member is the polar lipid.

8. The wound-healing composition of claim 1, wherein the fusion rate is at least $10^3$ vesicle fusions/second.

9. The wound-healing composition of claim 1, wherein the fusion rate is at least $10^6$ vesicle fusions/second.

10. A wound-healing composition, comprising:
at least one member selected from the group consisting of an antiseptic, an antibiotic, and an anesthetic; and
fusogenic vesicles comprising:
ATP at a concentration of 1 mM to 50 mM,
DOPC, and
POPA, wherein a ratio of DOPC:POPA is 1:1 to 500:1.

11. The wound-healing composition of claim 10, wherein a ratio of DOPC:POPA is 10:1 to 100:1.

12. A wound-healing composition, comprising:
becaplermin; and
fusogenic vesicles comprising:
ATP at a concentration of 1 mM to 50 mM,
DOPC, and
POPA, wherein a ratio of DOPC:POPA is 1:1 to 500:1.

* * * * *